United States Patent [19]
Bottiroli et al.

[11] Patent Number: 6,036,941
[45] Date of Patent: Mar. 14, 2000

[54] FLUOROGENIC SUBSTRATES FOR DIAGNOSIS AND PHOTODYNAMIC TREATMENT OF TUMORS

[75] Inventors: Giovanni Bottiroli, Travaco' Siccomario; Anna Cleta Croce, Torrazza Coste; Piero Baglioni, Fiesole; Monica Monici, Florence, all of Italy

[73] Assignee: Consiglio Nazionale Delle Ricerche, Rome, Italy

[21] Appl. No.: 09/011,347

[22] PCT Filed: Jul. 19, 1996

[86] PCT No.: PCT/EP96/03201

§ 371 Date: May 11, 1998

§ 102(e) Date: May 11, 1998

[87] PCT Pub. No.: WO97/03697

PCT Pub. Date: Feb. 6, 1997

[30] Foreign Application Priority Data

Jul. 19, 1995 [IT] Italy .................................. MI95A1560

[51] Int. Cl.[7] .................................................. A61K 49/00
[52] U.S. Cl. ............................................. 424/9.6; 600/317
[58] Field of Search ...................... 424/9.6, 9.61; 514/383, 454; 549/33, 223, 224, 228, 393; 560/8; 562/461; 435/968; 436/172, 800; 600/317

[56] References Cited

U.S. PATENT DOCUMENTS

| | | | |
|---|---|---|---|
| 4,647,367 | 3/1987 | Urban et al. ........................ | 208/48 AA |
| 4,924,009 | 5/1990 | Neckers et al. ......................... | 549/223 |
| 5,137,800 | 8/1992 | Neckers et al. ....................... | 430/281.1 |
| 5,506,271 | 4/1996 | Meruelo et al. ......................... | 514/732 |
| 5,616,719 | 4/1997 | Davalian et al. ....................... | 546/334 |

OTHER PUBLICATIONS

Photochemistry and Photobiology, vol. 45, No. 6, pp. 879–889 (1987), "Photosensitizers: Therapy and Detection of Malignant Tumors", Dougherty et al.

American Society for Laser Medicine and Surgery Abstracts, 6, pp. 258–265 (1986).

Photochemistry and Photobiology, vol. 58, No. 6, pp. 895–900 (1993), "Yearly Review—Photodynamic Therapy".

J. Natl. Can. Inst., vol. 80, No. 20, pp. 1584–1585 (1988), "Photodynamic Therapy—Lots of Questions But Presently Few Answers", Eli Glatstein.

Photodynamic Therapy of Neoplastic Disease, Kessek, D. Ed., vol. 2, CRC Press, pp. 79–101 (1990), "Selective Localization of Photosensitizers in Tumors: A Review of the Phenomenon and Possible Mechanisms", Chi–Wei Lin.

Trends in Biotechnology, vol. 13, pp. 14–18 (1995), "Photodynamic Therapy", Julia G. Levy.

*Primary Examiner*—Jose' G. Dees
*Assistant Examiner*—Michael G. Hartley
*Attorney, Agent, or Firm*—Hedman, Gibson & Costigan, P.C.

[57] ABSTRACT

Fluorogenic substrates susceptible of fluorescence emission and photosensitization by enzyme transformation suitable for diagnosis and photodynamic treatment of tumors, consisting of fluorescent substances with photosensitization activity, chemically modified with a group quenching the fluorescence and photosensitization properties, the said quencher group being removable by the cell enzyme activity with restoration of the properties of fluorescence and photosensitization activity of the original substance.

5 Claims, 6 Drawing Sheets

FLUOROGENIC SUBSTRATES FOR DIAGNOSIS AND PHOTODYNAMIC TREATMENT OF TUMORS

This application is a 371 of PCT/EP96/03201, filed Jul. 19, 1996.

Fluorescent substances with photosensitizing activity are known which are able to locate themselves in preferably the tumour tissues and which are suitable for the diagnosis and photodynamic treatment of tumours (T. J. Dougherty: Photosensitizers: Therapy and detection of malignant tumours. Photochem. Photobiol., 45, 879–889, 1987).

The diagnosis is based on the fact that by excitation at an appropriate wavelength tumour mass is distinguished from the surrounding healthy tissue by virtue of the more intense emission of fluorescence as a consequence of a greater quantity of the fluorescent photosensitising substance accumulated in tumour.

The photodynamic treatment is based on activation of the above-mentioned substance by irradiation with light of appropriate wavelength, with the production of highly toxic species (singlet oxygen, obtained by transfer of energy from the fluorescent photosensitizer in the triplet state) which cause irreversible damage to the biological tissue which contains those substances, with consequent necrosis (J. G. Parker: Optical detection of the photodynamic production of singlet oxygen in vivo. Laser Surg. Med., 6, 258–265,1986).

Among the numerous substances able to ensure an adequate photodynamic yield, particular attention has been paid to the porphyrin derivatives which are currently used in clinical practice for treating tumours of various kinds (T. J. Dougherty: Photodynamic Therapy. Photochem. Photobiol., 58, 895–900, 1983). In particular, two substances are the most widely used, both derived from hematoporphyrin by chemical treatment and known as HpD (Hematoporphyrin-derivative) and Photofrin®.

The use of acetoxymethyl esters of pH-sensitive amphipathic photosensitizers for photodynamic therapy involving endocytosis of lipophilic carriers leading to lysosomal uptake of the esterified photosensitizers by target cells has been proposed. Some esters of pheophorbide a and of chlorin e6 have been tested under in vitro conditions but not uniform results have been obtained. In fact, in contrast to the ability of chlorin e6 triacetoxymethyl ester and pheophorbide a acetoxymethyl ester to serve as a substrate for lysosomal enzymes, both methyl and phytyl esters of pheophorbide a were untouched by the esterases (D. Sahai et al., Photochem. and Photobiol., 58, 6, 803–808,1993).

Notwithstanding the validity of the premises on which they are based, fluorescence diagnosis and photodynamic therapy have notable limitations, as specified below.

The gradient of concentration of the fluorescent photosensitising substance between the tumour and the healthy tissue often is not sufficient to show the tumour mass with sufficient distinctness and to activate an efficacious photodynamic action. In particular, in the case of Photofrin® at the doses normally used (2.5–5 mg/Kg b.w.) the gradient of concentration between tumour tissue and the surrounding healthy tissue is such as to require careful dosing of the light to avoid undesirable side effects to the healthy part of the organ.

Further, the cutaneous photosensitization deriving from the need to use relatively high doses of the drug to obtain acceptable gradients of concentration between tumour tissue and normal tissue, imposes the need to avoid exposing the patients to any light source.

At the root of the objective difficulty of optimising photodynamic treatment, numerous problems can be identified, concerning in particular the exact definition of the modalities of interaction between the fluorescent photosensitising substance and the biological substrate leading to the preferential drug accumulation in tumour, and of the biological mechanisms which lead to the necrosis of the tumour mass (Eli Glastein: Photodynamic Therapy—Lots of questions but presently few answers. J. Natl. Cancer Inst., 80, 1584–1585, 1988; Chi-Wei Lin: Selective localisation of photosensitizers in tumours: review of the phenomenon and possible mechanism. In: Photodynamic therapy of neoplastic disease. D. Kessel ed.; vol. 2, CRC Press, pp. 79–101, 1990).

Other groups of fluorescent photosensitising substances (for example, phthalocyanines and benzoporphyrins) are currently being studied with the aim of both improving the intrinsic efficacy of the substance in the tumour mass, thus reducing the administered dose, and of involving larger quantities of tumour mass in the treatment by irradiation at wavelengths with a greater capacity for penetrating the tissues (J. J. Levi: Photodynamic Therapy. Trends in Biotechnology, 13, 14–18, 1995). The degree of penetration in the biological tissues of the light needed to activate the photodynamic process is in fact critical. For example, the absorption band of the porphyrin derivatives currently in use, positioned at about 600–630 nm, permits the involvement in the photodynamic process of layers of tissue not more than 5–7 mm thick.

SUMMARY

We have now found fluorogenic substrates susceptible of fluorescence emission and photosensitisation by enzyme transformation, which make it possible to obtain improved and unforeseen results in the diagnosis and photodynamic treatment of tumours.

These substrates consist of fluorescent substances with photosensitisation activity chemically modified with a group that quenches the properties of fluorescence and photosensitisation activity, this quencher group being removable by the specific enzyme activity, preferentially present in the tumour cells, with restoration of the properties of fluorescence and the photosensitisation activity of the original substance.

The choice of the quencher group according to the biological characteristics of the tumour, with particular regard to the enzyme activities, permits a remarkable increase of the amount of the active substance in the tumour cells in comparison with that in the surrounding healthy cells, with a greatly increased diagnostic and therapeutic effect.

DETAILED DESCRIPTION OF THE INVENTION

The characteristics and advantages of the fluorogenic substrates susceptible of fluorescence emission and photosensitisation by enzyme transformation according to the present invention are further illustrated in the following detailed description.

Fluorogenic substrates in the present invention are derivates of xanthenes, porphyrins, phthalocyanines, chlorines and peri-hydroxilated polycyclic quinones, containing quencher groups such as for example the acetate, sulphate, phosphate, dibutyryl ester, galacto-pyranoside, glucoronide, acetamide-dioxyglucopyranoside groups, respectively recognisable by the enzymes: esterase, sulphatase, phosphatase, lipase, β-galactosidase, β-glucoronidase, and glucosoaminidase.

These quencher groups have the characteristic of suppressing the properties of fluorescence and the photosensitisation activity of the molecules in which they are introduced, and of being removed by the specific enzyme activity, preferentially present in the tumour cells, when the substance has been incorporated in the cells.

Thus the quencher groups transform an active substance into an inactive substance while the enzyme activity restores the active substance. The above-mentioned substrates can be used with advantage in the diagnosis and photodynamic therapy of tumours.

Information is reported below about experiments performed using as fluorogenic substrate Rose Bengal acetate, which belongs to the group of xanthene derivatives.

Similar results, however, have been obtained with a significant number of the substrates mentioned above.

The Rose Bengal has the following chemical structure:

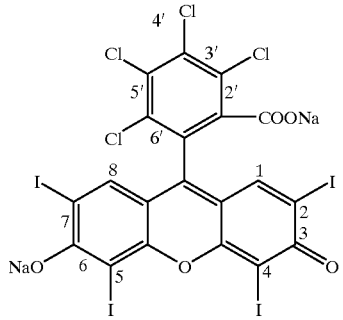

Rose Bengal modified with the acetate quencher group according to the present invention has the following chemical structure:

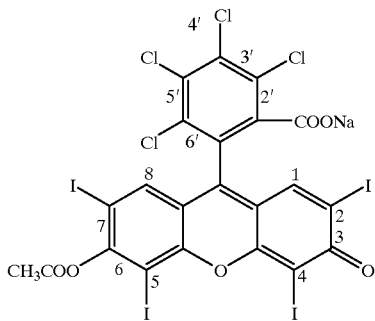

Preparation of Rose Bengal acetate

Rose Bengal acetate was prepared by the following method.

1 gr. of Rose Bengal (Sigma Chem. Co., St. Louis, Mo., USA) was put in 50 ml of acetic anhydride and kept in agitation for 16 h. The slow fading of the fuchsia colour, typical of Rose Bengal, to a pale pink hue, indicated the proceeding of the reaction. The reaction mixture was treated in the end with NaOH diluted in water, and the product was extracted with ethyl acetate and recrystallised twice with ethanol.

Figure 1:
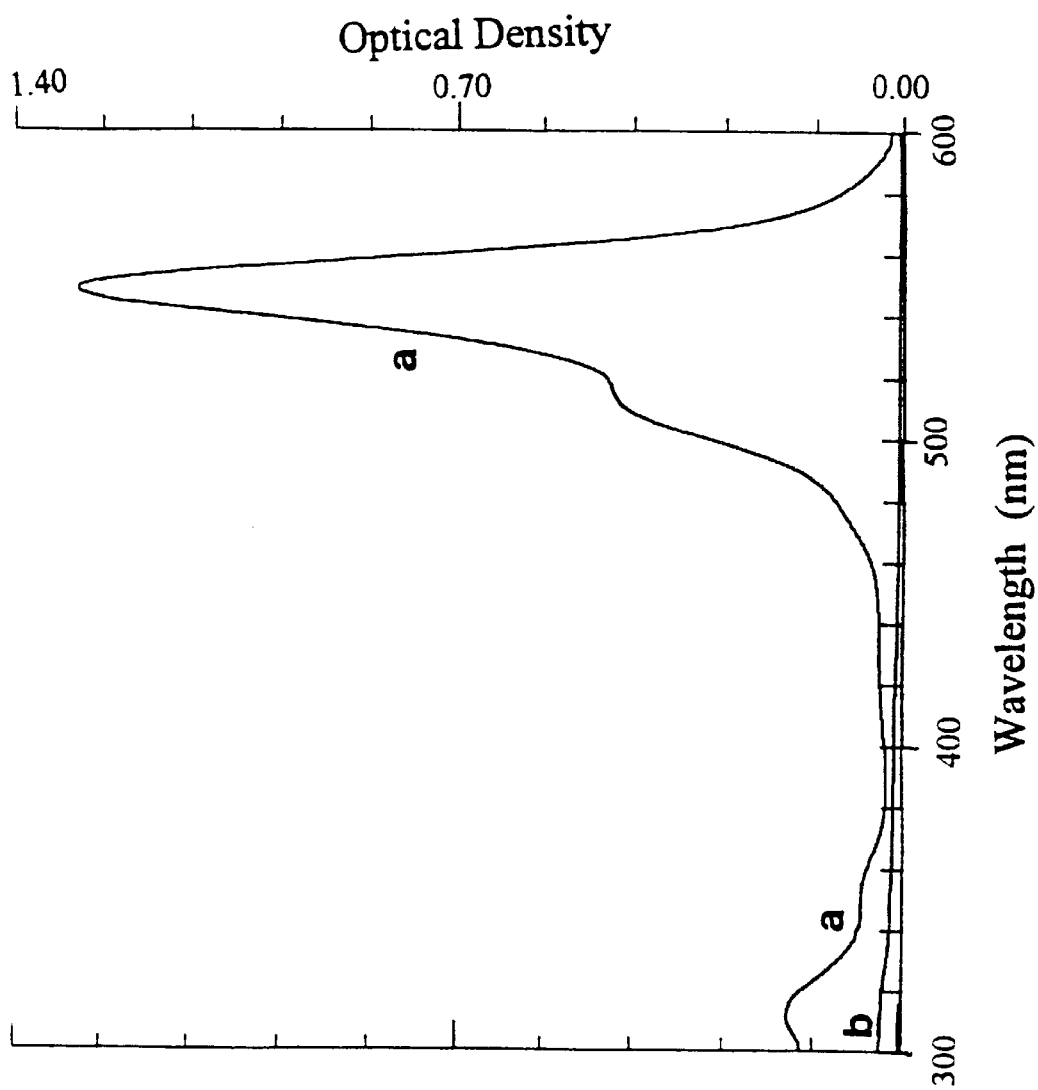
FIG. 1 shows the absortion spectrum of Rose Bengal at the concentration of $10^{-5}$ M (curve a) and the absorption spectrum of Rose Bengal acetate at the concentration of $10^{-4}$ M (curve b).

The introduction of the acetate group in the molecule of the Rose Bengal, perturbing the double-bond conjugation system of the chromophore, determines the disappearance of colour from the substance with consequent modification of the absorption spectrum: the absorption band at about 530 nm disappears, while the band in the middle of the UV (310nm) is notably reduced, as is shown in FIG. 1, in which the curve (a) refers to the absorption spectrum of Rose Bengal at the concentration of $10^{-5}$ M, and the curve (b) refers to the absorption spectrum of Rose Bengal acetate at the concentration of $10^{-4}$ M, in the interval 300–600 nm.

Figure 2:
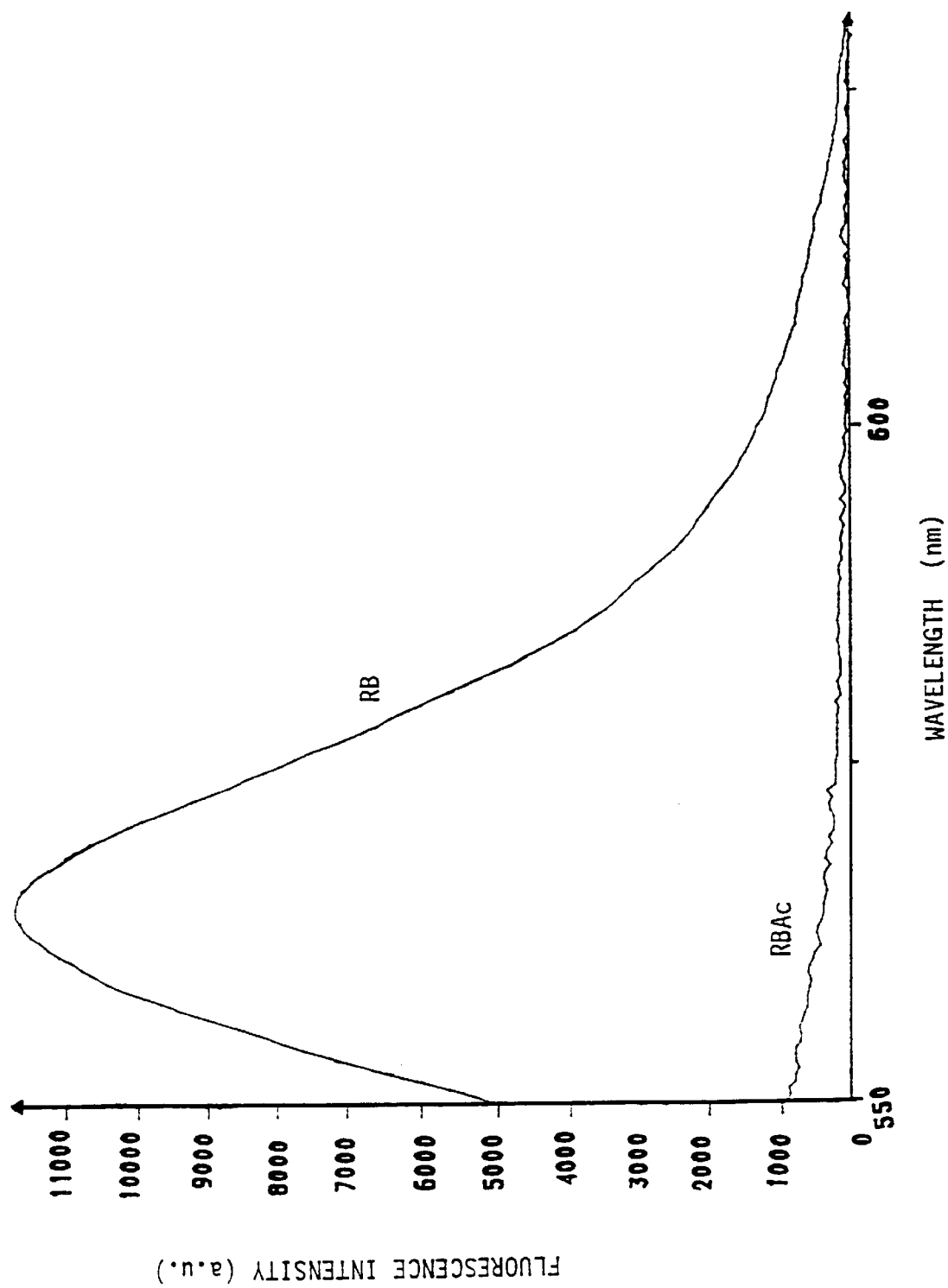
FIG. 2 shows that the Rose Bengal acetate (RBAc) loses the fluorescence properties.

At the same time Rose Bengal acetate loses completely the fluorescence properties, as shown in FIG. 2, in which RB indicates Rose Bengal and RBAc indicates Rose Bengal acetate.

The curves of FIG. 2 refer to the fluorescence emission spectra in the interval 550–650 nm, by excitation at 525 nm at the concentrations $10^{-6}$ M for RB and $10^{-4}$ M for RBAc.

Pharmacological experimentation

The Rose Bengal acetate prepared as described above was submitted to enzyme hydrolysis in the presence of esterase, which is an enzyme particularly present in tumour cells.

To the solution of Rose Bengal acetate $3\times10^{-5}$ M in phosphate buffer 0.2 M (pH 6.85) was added the purified esterase enzyme of pig liver (Sigma Chem, Co., GB) at the final concentration of 25 U/ml. The reaction was performed at room temperature (20° C.) and the formation of the product was measured fluorometrically (excitation 525 nm, emission 565 nm). In a second group of experiments, to the reaction solution was added human albumin (Sigma Chem. Co, GB) at the concentration of 0.1 mg/ml, better to simulate the conditions of hydrophobicity to be met in the cells. In these conditions, the appearance of the fluorescence was accelerated.

The emission spectrum of the product of the enzyme reaction corresponds perfectly to that of Rose Bengal, and this demonstrates that the hydrolysis restores the structure of the active substance by removal of the quencher group.

Figure 3:
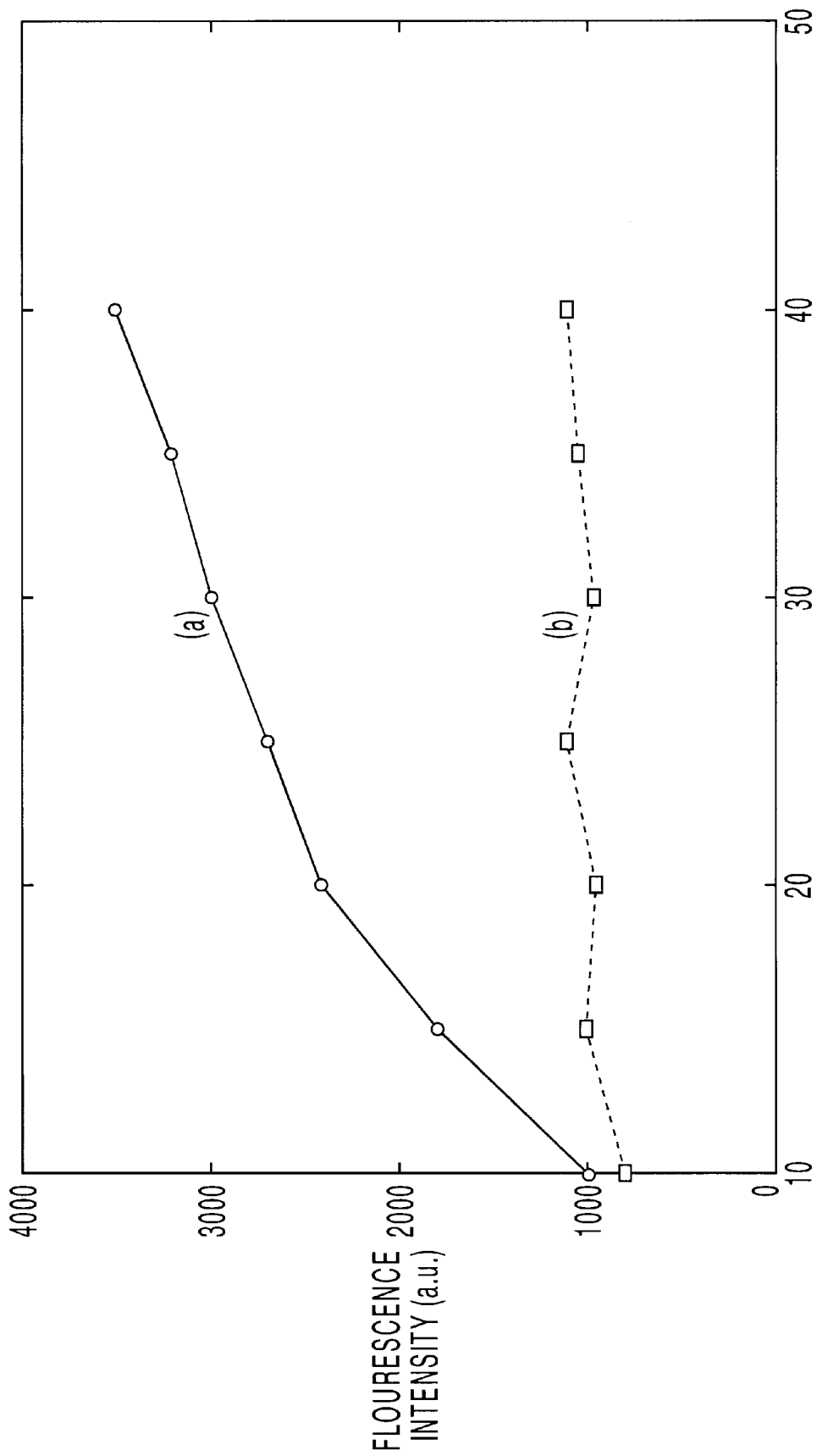
FIG. 3 shows the intensity of fluorescence of Rose Bengal acetate subjected to hydrolysis in the presence of albumin with esterase (curve a) and the intensity of fluorescence of the solution of Rose Bengal acetate with albumin in the absence of esterase (curve b)

The kinetics of hydrolysis was followed by determining the intensity of fluorescence at 565 nm corresponding to the peak of emission of Rose Bengal. Examples of curves of hydrolysis kinetics are shown in FIG. 3 in which the curve (a) represents the intensity of fluorescence in time of a solution of Rose Bengal acetate subjected to hydrolysis in the presence of albumin with esterase, and the curve (b) represent the intensity of fluorescence of the solution of Rose Bengal acetate with albumin, in the absence of esterase, at the concentration of $3\times10^{-5}$ M.

Measurements performed on solutions at different concentrations made it possible to estimate a value of the enzyme hydrolysis constant Km of the order of $10^{-3}$ M. The reaction does not seem particularly rapid considering that in the same conditions the Km for diacetate fluorescein is about 3 orders of magnitude greater ($5\times10^{-6}$ M).

Evaluations of the kinetics of intracellular accumulation of Rose Bengal acetate were performed on cultures of an established cell line of rat glioma (C6) which grows as a monolayer. This cell line is widely used for pharmacokinetic studies of fluorescent substances with photosensitisation activity by virtue of its rapid proliferation activity and the possibility of modifying the physiological activities of the cells.

Figure 4:
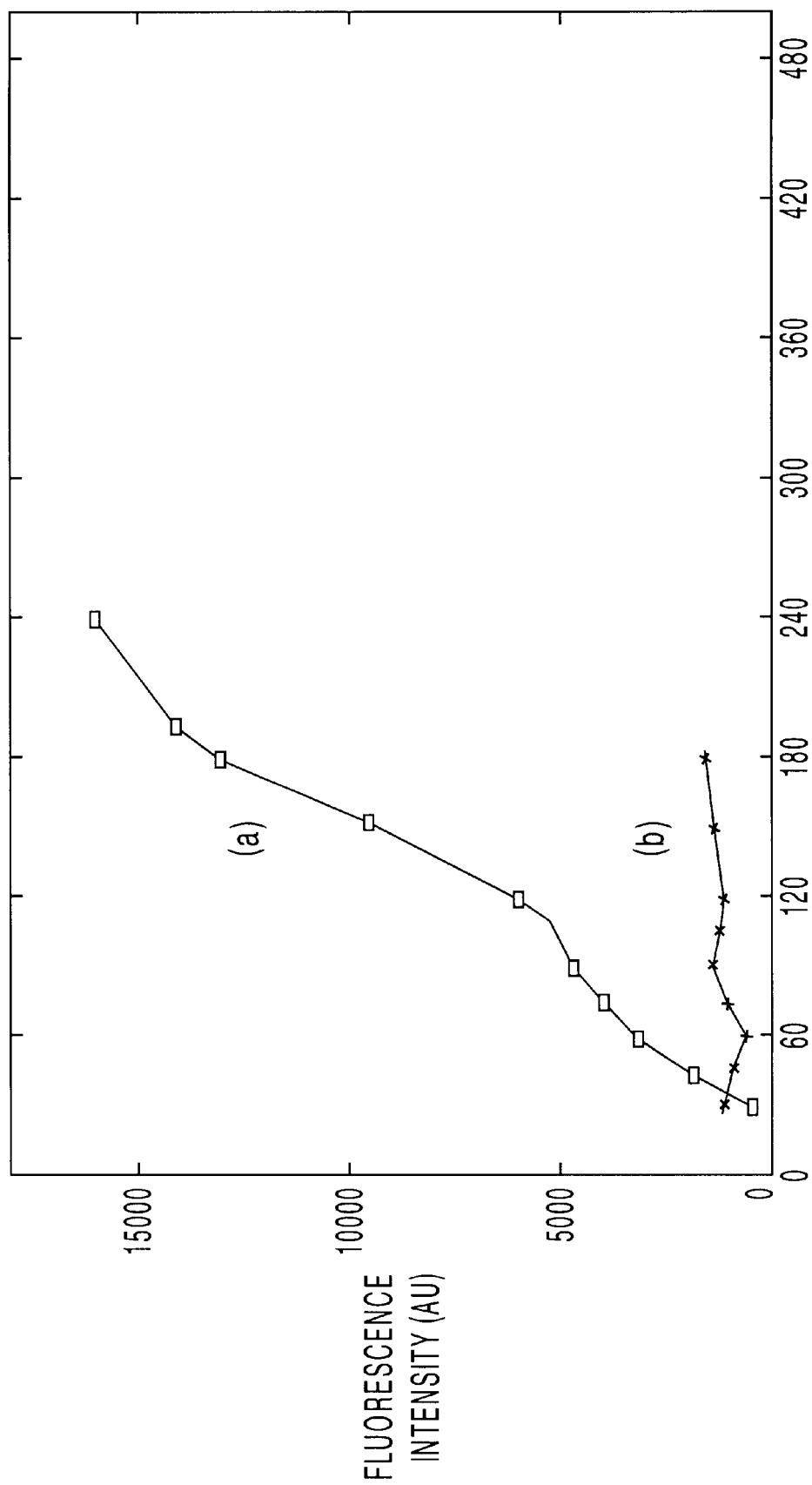
FIG. 4 shows the quantity of Rose Bengal accumulated in the cells when administered in the acetylated form (curve a), and in the non-acetylated form (curve b)

The treatments, performed in D-MEM medium (Minimum Essential Medium, modified according to Dulbecco (E. Dulbecco and G. Freeman. Virology 8, 396, 1959), with the addition of foetal calf serum (10%), concerned the range of concentrations from $1\times10^{-6}$ to $1.5\times10^{-5}$ M both for Rose Bengal and for Rose Bengal diacetate. The kinetics of accumulation was followed as an increase in time of the intensity of fluorescence measured as the peak (580±5 nm) of emission of Rose Bengal. Preliminary measurements by microspectrofluorometry had indicated that also in the case of intracellular hydrolysis the species liberated corresponds to Rose Bengal. The curves of uptake for the two species are illustrated in FIG. 4, which shows that the quantity of Rose Bengal accumulated in the cells is notably greater in the case of the substance administered in the acetylated form (curve (a)) than in the non-acetylated form (curve (b)). It is particularly important that, principally in short-term treatments, a continuous increase of intracellular Rose Bengal is recorded in the cells treated with the acetylated species, even when the cells are transferred into a medium devoid of this substance. This can easily be interpreted in terms of the balance between the processes of incorporation and hydrolysis. Since the process of incorporation is rapider than that of hydrolysis, inside the cells an accumulation is created of hydrolysable substance on which the enzyme can continue to effect its action through time.

Further, it is interesting to note that the kinetics of hydrolysis of Rose Bengal acetate is accelerated by the cellular environment: the Km passes from about $10^{-3}$ M in conditions of hydrolysis in solution to about $10^{-6}$ M in the cells.

The hydrophobicity of the intracellular environment would therefore seem to create the structural condition that favours the action of the enzyme. It is also interesting that the two substances give rise to very different fluorescence pictures: in the case of treatment with Rose Bengal the localisation is limited to the cellular membrane, in agreement with the physico-chemical characteristics (A. C. Croce, E. Wyroba, G. Bottiroli, J. Photochem Photobiol., B. Biol., 16, 319, 1992); when Rose Bengal acetate is used the fluorescent substance liberated inside the cell appears in all the cellular compartments except the nucleus, with perinuclear polar distribution in agreement with the localisation typical of lysosomes. Tests of cellular vitality performed with the trypan blue and fluorescein diacetate methods have shown that with incubation for 4 h at concentrations up to $1\times10^{-4}$ M there is no significant cell mortality for Rose Bengal acetate or for Rose Bengal. The finding relative to Rose Bengal agrees with the literature (R. P. G. Feenstra and S. C. G. Tseng, Ophthalmology, 99 605, 1992).

The cells treated with Rose Bengal or with Rose Bengal acetate as described above were submitted to irradiation at 540±5 nm by a Xe 75 W lamp and an interference filter.

Figure 5:
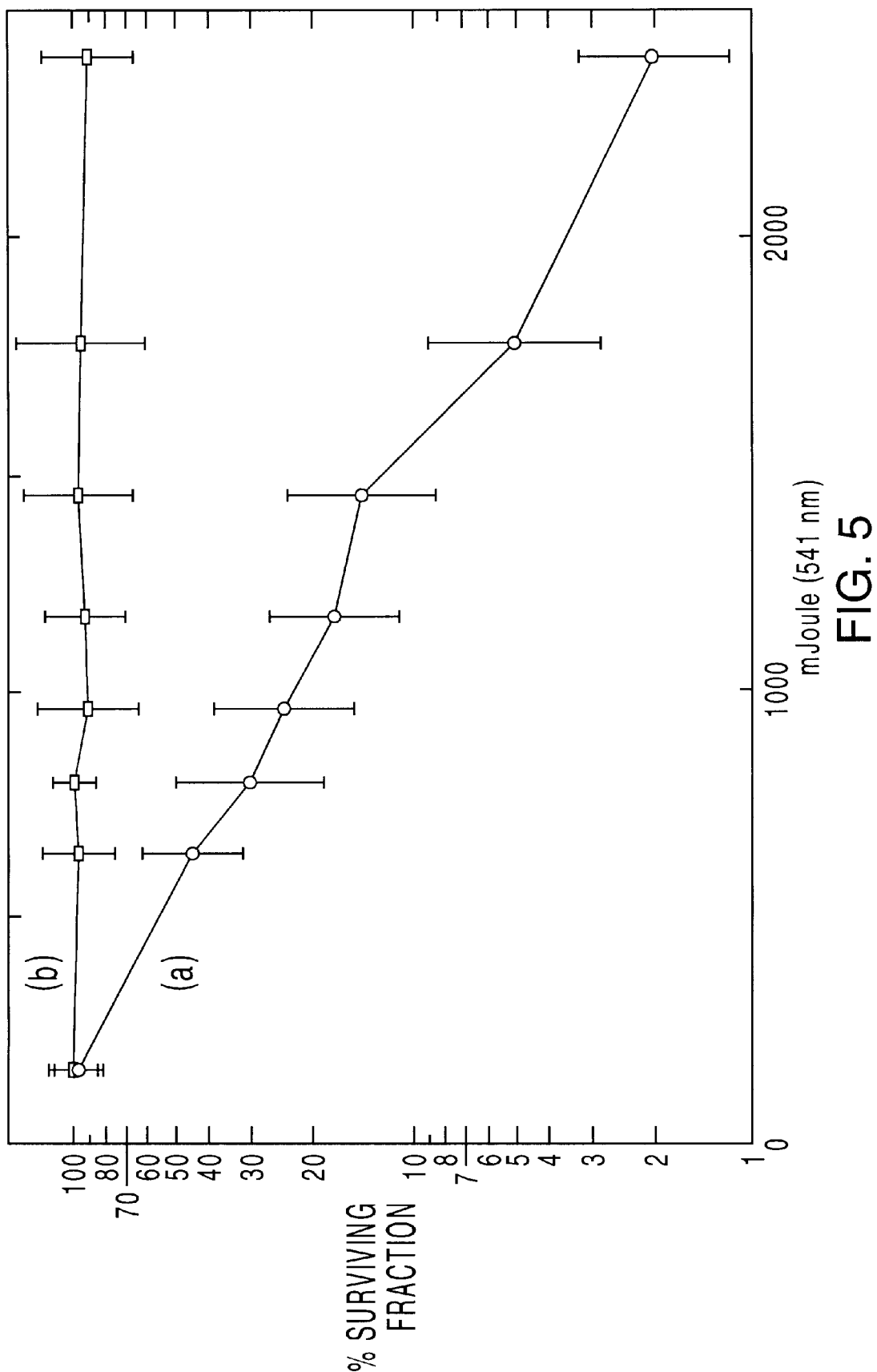
FIG. 5 shows the cell survival curves in the treatment with Rose Bengal acetate (curve a) and in the treatment with Rose Bengal (curve b)

Irradiation was realised with a power of 2 mw/cm$^2$ for various times until the administration of a maximum dose of 2.4 J, in accordance with the protocols normally used in tests of phototoxicity. The irradiation was effected in HBSS buffer (Hank's Balanced Salt Solution, J. H. Hanks and R. E. Wallace, Proc. Natl. Exp. Biol. Med 71, 196, 1949) in the absence of the drug in the culture medium to avoid secondary effects. Twenty-four hours after irradiation the cells adhering to the slide on which they had been grown were counted. The expression of phototoxicity was defined as the ratio between the number of cells present after the treatment and those counted on the untreated controls. FIG. 5 shows the cell survival curves so calculated, evidencing a strong phototoxic effect in the case of treatment with Rose Bengal acetate (curve (a)) as compared with Rose Bengal (curve (b)). This effect relates directly to the quantity of fluorescent substance with photosensitisation activity produced by the enzyme activity, evaluated as fluorescence intensity at 580 nm (FIG. 4).

A comparison of intracellular drug accumulation was made between normal and tumour cells. As a model, a normal fibroblast line from embryos (6–10 days) of Galliera strain rats, and a stabilised cell line derived from sarcoma spontaneously growing in syngeneic Galliera rats, were used. After incubation with Rose Bengal acetate at a concentration of $5\times10^{-6}$ M for 2 hours, a ratio of intracellular photosensitizer concentration of about 16 was measured between normal and transformed cells, in terms of fluorescence intensity at 580 nm. The ratio of the esterase activity in the two cell lines was found less than the ratio shown by the photosensitizer: this can be explained by the fact that the Rose Bengal produced by the enzyme activity is a polar compound. It must be considered that in this form Rose Bengal requires an active transport mechanism to be released (E. Prosperi, A. C. Croce et al. Cytometry, 7, 70–75, 1986), and that the tumour cells are characterised by an impaired metabolic condition (J. Szollosi, P. Kertai et al. J. Histochem. Cytochem. 29, 503–510, 1982), that enhances the photosensitizer accumulation.

Figure 6:
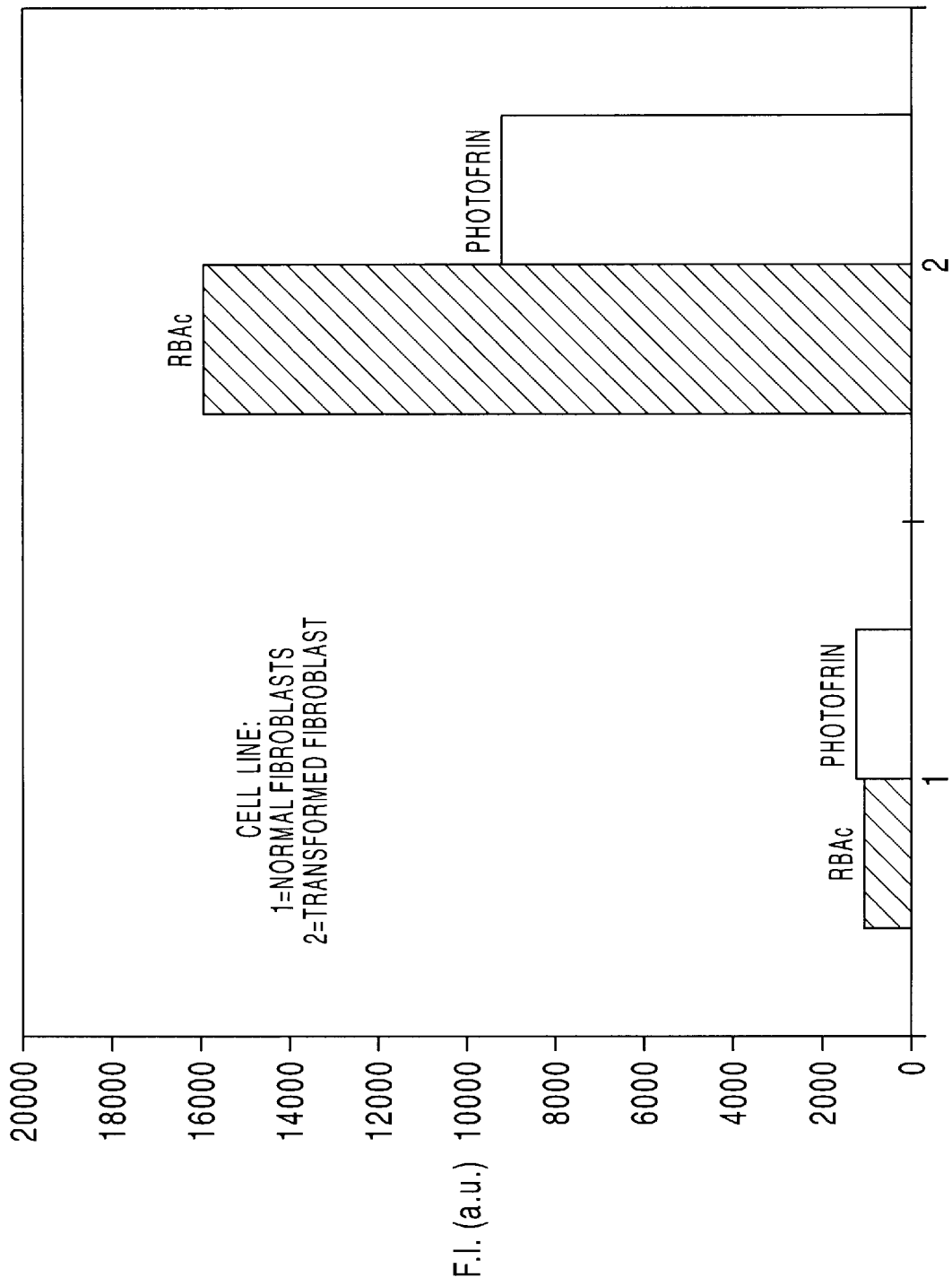
FIG. 6 shows the intracellular concentration of Rose Bengal acetate (RBAc) in comparison with a commonly used photosensitizer (Photofrin®).

The same cell lines, treated with the most commonly used photosensitizer, Photofrin®, at the concentration of $2\times10^{-5}$ M for a time of 2 hours yielded a ratio value of about 8 (FIG. 6).

Tests were also performed on cell lines derived from human tumours: POGB, from bronchial microcytoma, and IGROV, from ovarian carcinoma. In particular, for each line a comparison was made between the cells sensitive and resistant to chemotherapeutic agents. The drug resistance is one of the major causes of the failure of tumour chemotherapy, and was proved to affect strongly the accumulation of photosensitizers. Results related to Rose Bengal treatment were compared with those obtained with Photofrin®, a well-establishes photosensitizer.

The cells were treated with Rose Bengal acetate at doses between $5\times10^{-5}$ and $10^{-7}$ M, and with $10^{-5}$ M Photofrin®. The intracellular accumulation of photosensitizer was evaluated in terms of fluorescence intensity. Giving a value of 100 to the photosensitizer amount present in each sensitive cell line, the amount of photosensitizer retained in the corresponding resistant cell line is 100% and 85% for Photofrin and 170% and 120% for Rose Bengal, in IGROV and POGB respectively. A more evident difference of the accumulation capacity between Photofrin and Rose Bengal can be observed in the case of B16 cells, a line derived from mouse melanoma. In this case the amount of Photofrin® accumulated in resistant cells is about 65% of that in sensitive ones, while the amount of Rose Bengal is about 120%.

The results are explicable by the intracellular production of active Rose Bengal following to the accumulation of fluorogenic substrate balancing the drug efflux related to the drug resistance mechanism.

The results indicate that the intracellular accumulation process of Rose Bengal in the active form, after treatment with the fluorogenic substrate Rose Bengal acetate, is modulated by the cellular expression of the specific enzyme activity, and, moreover, is favoured by an impairment of the active transport mechanism that regulates the drug efflux.

Considering the possible systemic use of Rose Bengal acetate, the effect was evaluated of the serum esterase activity on the hydrolysis kinetics of the fluorogenic substrate. The esterase activity of the blood can induce an extracellular hydrolysis of Rose Bengal acetate. The kinetics, however, of this hydrolysis is slow enough to permit the cellular compartment to accumulate and hydrolyse the Rose Bengal acetate according to the intracellular esterase activity. In any case the hydrolysed Rose Bengal is quickly eliminated from the blood. Samples taken from Swiss mice treated with 8 mg/kg of Rose Bengal acetate do not present appreciable quantities of Rose Bengal in the blood, according to the literature ( H. K. Wang, S. Miyachi et Al, Biopharmaceutics and Drug Deposition, 13, 647, 1992).

In regard to the white blood cells, the lymphocytes showed a capacity to hydrolyse Rose Bengal acetate, according to the esterase activity of the cell types considered. Experiments performed on smears showed hydrolysis activity of Rose Bengal acetate in lymphocytes 40% less than in granulocytes.

Tests on nude mice, bearers of experimental tumours derived from the human tumour cell lines described above, have yielded results in agreement with those obtained on the corresponding lines.

Results similar to those of Rose Bengal acetate have been obtained with numerous other fluorogenic substrates according to the present invention: in particular with Rose Bengal phosphate, Rose Bengal mono-butyrate, Rose Bengal di-butyrate, hematoporphyrin mono- and di-acetate, hematoporphyrin phosphate, protoporphyrin IX mono- and di-acetate, protoporphyrin IX phosphate, phthalocyanine mono- and di-acetate, phthalocyanine phosphate, hypericin poly-acetate and hypericin poly-phosphate.

The experimentation described above thus demonstrate that the fluorogenic substrates according to the present invention are easily incorporated inside the cells, that they have an intrinsic toxicity no greater than that of the original active substance and that, once incorporated in the cells, they undergo enzyme hydrolysis with liberation of the active substance which remains inside the cells much longer than is necessary for activation of the procedure of irradiation needed for the production of the toxic species.

As against the traditional photodynamic therapy, based on the direct use of fluorescent photosensitising substances, the fluorogenic substrates in the present invention have the advantage of permitting therapeutic treatment better rationalised in that it can be planned on the basis of the biological differences between tumour tissue and healthy tissue.

In fact, on the basis of the biological characteristics of a determined type of tumour it is possible to identify the quencher group towards which the tumour expresses the specific enzyme to a greater extent than the healthy tissue. The increase of specificity deriving from this, as well as improving notably the efficacy of the treatment, furnishes the possibility of reducing markedly the doses to administer, with consequent elimination of the side effects due to aspecific distribution of the drug.

Further, the choice of the quencher group according to the biological characteristics of the tumour greatly increases the capacity to load tumour cells with the substance selectively, as against the surrounding healthy cells. This results in an increase also of the potentiality of the active substance for diagnostic purposes, through the increase of the drug/background fluorescence signal ratio.

The advantages deriving from the use of fluorogenic substrates in the present invention thus constitute the condition for the optimisation on a rational basis of diagnosis and photodynamic therapy in oncology. Applications are foreseeable in all the sectors for which photodynamic therapy is currently proposed, with particular reference to cavity tumours where the use of optic fibre systems associated with endoscopy to achieve conditions of irradiation permits a minimally invasive therapeutic approach.

Further, applications are foreseeable to cell suspension as in the case of hematic pathologies and of the purging of bone marrow for autologous transplantation.

The fluorogenic substrates in the present invention can thus be used for the preparation of pharmaceutical compounds for fluorescence diagnosis and for photodynamic therapy of tumours, composed of an efficacious quantity of at least one of the above-mentioned substrates mixed with compatible solvents and excipients normally used in pharmaceuticals.

The invention also includes the diagnostic method and the therapeutic method for tumours consisting in giving the patients an efficacious quantity of at least one fluorogenic substrate according to the present invention and in irradiating the part concerned with radiation at wavelengths in the interval 400–800 nm, depending on the spectral properties of the compound used, on the aim of its use and, in the case of therapy, on the thickness of the tissue it is required to treat.

The dose of substrate to administer varies from 1 to 10 mg/kg b.w. The administration can be systemic in the form of an isotonic saline solution obtained by dilution of at least 1: 1000 of stock solution of substrate in dimethylsulfoxide, or as a suspension of liposomes.

The same preparation can be administered by the intracavitary route.

Topical application requires the use of water solution with the addition of substances favouring the absorption and penetration of the active principle (for example, solution of isopropanol:water:azone(N-dodecylazacyclopentan-2-one) in the ratio 50:48:2).

We claim:

1. A method for the diagnosis of tumors comprising administering an effective amount of at least one fluorescent substance chemically modified by introducing a quench group that quenches the properties of fluorescence and photosensitisation activity of said substance, said quencher being removable by enzyme activity of tumor cells with restoration of the properties of fluorescence and photosensitization activity of the unmodified substance to form a photosensitized biological substance by irradiating an involved part of the body with radiation at wavelengths between 400 nm and 800 nm and thereafter determining the presence of a tumor by detecting an increase in fluorescence wherein the chemically modified fluorescent substance is selected from the group consisting of Rose Bengal acetate, Rose Bengal phosphate, Rose Bengal monobutyrate and Rose Bengal dibutyrate.

2. A method according to claim 1, wherein said chemically modified fluorescent substance consists of Rose Bengal acetate.

3. A method according to claim 1, wherein said chemically modified fluorescent substance consists of Rose Bengal Phosphate.

4. A method according to claim 1, wherein said chemically modified fluorescent substance consists of Rose Bengal monobutyrate.

5. A method according to claim 1, wherein said chemically modified fluorescent substance consists of Rose Bengal dibutyrate.

* * * * *